(12) United States Patent
Emmrich et al.

(10) Patent No.: US 8,067,019 B2
(45) Date of Patent: Nov. 29, 2011

(54) WAX TREATED BURNABLE DISPENSING SUBSTRATES

(75) Inventors: Robert R. Emmrich, Racine, WI (US); Robert D. Iverson, Racine, WI (US); Russell O. Carlsen, Racine, WI (US); Patrick J. McCray, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 341 days.

(21) Appl. No.: 12/420,975

(22) Filed: Apr. 9, 2009

(65) Prior Publication Data

US 2010/0260814 A1 Oct. 14, 2010

(51) Int. Cl.
*A01N 25/34* (2006.01)
*A01N 25/00* (2006.01)

(52) U.S. Cl. .................................. 424/414; 424/405

(58) Field of Classification Search ...................... None
See application file for complete search history.

(56) References Cited

U.S. PATENT DOCUMENTS

| | | | | |
|---|---|---|---|---|
| 2,698,309 | A * | 12/1954 | Thwaites et al. | 524/585 |
| 3,295,246 | A * | 1/1967 | Landsman et al. | 43/131 |
| 3,730,674 | A * | 5/1973 | Gross | 431/288 |
| 4,144,318 | A | 3/1979 | D'Orazio | |
| 4,449,987 | A | 5/1984 | Lindauer | |
| 4,790,747 | A * | 12/1988 | O'Brien | 431/325 |
| 4,797,090 | A * | 1/1989 | Rogers | 431/290 |
| 5,023,134 | A * | 6/1991 | Bezigian et al. | 428/336 |
| 5,447,713 | A * | 9/1995 | Elsner et al. | 424/40 |
| 5,657,574 | A | 8/1997 | Kandathil et al. | |
| 5,688,509 | A * | 11/1997 | Radwan et al. | 424/736 |
| 5,876,706 | A | 3/1999 | Zaunbrecher | |
| 5,948,424 | A | 9/1999 | Kandathil et al. | |
| 6,371,755 | B1 | 4/2002 | Dearth | |
| 6,419,898 | B1 * | 7/2002 | Flashinski et al. | 424/40 |
| 6,732,473 | B2 * | 5/2004 | Geyer et al. | 43/125 |
| 6,941,697 | B2 | 9/2005 | Arya | |
| 2007/0003586 | A1 * | 1/2007 | Homoelle et al. | 424/405 |

FOREIGN PATENT DOCUMENTS

WO 2010031508 A2 3/2010

OTHER PUBLICATIONS

PCT/US2010/001061 International Search Report dated Apr. 21, 2011.

* cited by examiner

*Primary Examiner* — Robert A Wax
*Assistant Examiner* — Olga V Tcherkasskaya

(57) ABSTRACT

Disclosed herein are burnable air treatment chemical dispensing substrates, such as mosquito coils, in which wax is incorporated. In one form the wax portion is a separate coating layer in which the air treatment chemical is also placed. This permits the underlying base to be dried without loss of air treatment chemical. Methods for forming such coils are also disclosed.

10 Claims, 3 Drawing Sheets

WAX TREATED BURNABLE DISPENSING SUBSTRATES

CROSS-REFERENCE TO RELATED APPLICATIONS

Not applicable.

STATEMENT REGARDING FEDERALLY SPONSORED RESEARCH/DEVELOPMENT

Not applicable

BACKGROUND OF THE INVENTION

The present invention relates to burnable substrates such as mosquito coils for dispensing air treatment chemicals. More particularly it relates to ways of achieving desired air treatment effects using lower levels of air treatment chemicals.

Insect control ingredients, fragrances, and other air treatment chemicals have been dispensed into the air by a variety of types of dispensers. Some use an electrical heater to volatize the active into the air from a wick, mat, or other substrate. Others use a fan to blow active off of a porous substrate into the air.

Another approach is to use a burning device to dispense the active. For example, candles having wicks have had fragrance, citronella, and other air treatment chemicals mixed with their wax such that as the wax is consumed by the candle the active is dispensed.

Such candles have been formed in a variety of configurations. See eg. U.S. Pat. No. 6,371,755. However, this approach requires a burning flame (which is susceptible to being blown out, which restricts where the candle can be placed, and restricts the actives).

Still another approach is to use a burnable object which consumes itself without a flame. Insect control coils (e.g. "mosquito coils") and incense punks are of this type. They can be manufactured at very low cost (e.g. making them particularly suitable for use in impoverished countries that have severe malaria control issues).

Mosquito coils typically have a generally spiral-shaped body with is composed of a slowly burnable solid material that is impregnated or coated with an insect control active ingredient (such as a repellant, an insecticide, or an insect growth regulator). When the coil burns, the heat from the burning vaporizes and disperses the insect control active ingredient. Examples of such coils are disclosed in U.S. Pat. Nos. 4,144,318, 5,657,574, 5,948,424, 6,419,898, 6,732,473, and 6,941,697.

It is desirable that such a coil burn very slowly as such coils are often intended to provide protection for eight hours or so (e.g. overnight). Further, coil materials must be designed to be consumed so that they don't easily snuff out before the coil is used up and so that they don't readily burst into flames after the initial lighting. Another constraint is that they cannot be so brittle as to present undesirable breakage risks. This can be a significant consideration given the inherent nature of dough derived cellulosic materials and that such coils are often supported only at discrete positions (e.g. their centers) to reduce the risk of snuffing.

Further they must also be made of materials that don't interfere with the active in undesirable ways (e.g. react with the active during storage; retard dispensing of active too much). Also, any ingredient of the coil should not significantly increase the overall cost of the coil over standard ingredients, given that typical users of such coils are often extremely poor.

Such coils have therefore traditionally been made of largely cellulosic secondary/by product powder materials (e.g. coconut or peanut shell flour, sawdust, ground leaves, ground bark), sometimes with small amounts of additives that will affect burning characteristics or appearance, modify production characteristics, or act as a preservative (e.g. binder starch, kerosene, potassium chloride, or dye). While existing coils made from these materials have proven quite useful, there is a desire to improve them further.

For example, in order to achieve desired extended burn times using such conventional ingredients one must typically make the coil of a certain minimum size (which, if it could be reduced without cutting back on burning time could lead to cost savings and consumer preference). Also, many such coils are manufactured using wet extrusion followed by a drying step to create the desired rigidity. Some active can be prematurely volatized during the drying step, thereby increasing the cost of the active (as more needs to be added to achieve a given result during burning).

Further, many coils uniformly mix active throughout the coil. As a result, some of the active can be destroyed or partially degraded during the burning process before it is able to be dispensed. Also, because active will to some extent slowly volatize from standard coils in storage (absent precautions) they must be packaged in relatively expensive sealed packaging prior to use. This increases the cost of the ultimate product to the consumer.

Hence, a need exists for insect control coils which achieve improvements with respect to the above concerns.

BRIEF SUMMARY OF THE INVENTION

In one aspect the present invention provides an air treatment chemical dispensing substrate having a burnable body with at least 89% by weight of non-wax base material, between 0.05% and 10% by weight of wax, and an air treatment chemical to be dispensed by the substrate. Preferred air treatment chemicals are selected from the group consisting of pyrethroids, pyrethrum, insect-repelling natural volatile oils, insect growth regulators, and mixtures thereof, and fragrances. Metofluthrin or pynamin forte/d-allethrin are especially preferred when the substrate is for mosquito control.

The body is preferably in the form of a coil, such as a coil suitable to control mosquitoes. The coil is most preferably a spiral shaped essentially planar coil. However, the coil may take various top view forms other than circular spiral (e.g. rectangular spiral).

Insect "control" is defined to mean killing, repelling or otherwise altering the behavior of insects in a desired way. Altering insect behavior includes but is not limited to knocking insects down, repelling them, reducing their tendency to bite, altering reproduction or development, and the like. "Insect" is defined to include actual insects as well as arachnids and other small animals commonly controlled with insects, albeit the primary intended purpose at present is for mosquito control.

The non-wax main body is preferably mostly made of a cellulosic and/or charcoal-based material. In a very preferred form it is essentially free of wax, with the wax instead being coated on top of the main internal body. The air treatment chemical can be mixed throughout the main body, but much more preferably is included in a coating.

In one preferred form the substrate has at least 98% of non-wax base material which is cellulosic. For example, the base material could be formed from a paper sheet that has been cut into a coil shape.

The most preferred air treatment chemicals for controlling insects are present in at least 0.0001% by weight and is less than 2% by weight. Minimizing amounts of synthetic pyrethroids that is required is quite important given their relatively high cost as compared to the cost of the other materials in the coil.

For ease of application, it is preferred to apply the wax as part of a coating which is an emulsion containing at least wax, water and an emulsifier. This permits the wax coating to be quickly applied using automated procedures. The air treatment chemical can also preferably be mixed in with the emulsion, or otherwise applied as a coating.

To form such emulsions it is most preferred that the wax be selected from the group consisting of oxidized waxes such as oxidized polyethylene waxes and oxidized polypropylene waxes.

The final substrate can be formed by creating a wet version of an internal main body portion thereof, mostly drying that wet version, coating that at least partially dried wet version with a mixture of wax, air treatment chemical, surfactant and water to create a coated substrate, and then optionally further drying the coated substrate.

In another aspect there is provided by the present invention an insect control coil which has a burnable body having at least 89% by weight of non-wax base material, between 0.05% and 10% by weight of wax, and an insect control active to be dispensed by the substrate.

The present invention also provides methods for forming such dispensing coils/substrates which include forming a body comprising a cellulosic burnable base material and water, at least partially drying some water out of the body, then coating the at least partially dried body with an emulsion comprising water, surfactant, air treatment chemical/insect control active and wax, and then at least partially drying water out of the coating.

The addition of wax slows the burn rate, and can be presented without undesirably increasing the incidence of premature snuffing. The inclusion of the wax and the air treatment chemical in a separate coating layer permits the main body to be mostly dried before the air treatment chemical is added. Hence, there can be no loss of air treatment chemical during the main drying step. The same air treatment chemical effects can therefore be achieved with smaller coils/substrates, and/or with less air treatment chemical/insect control active added during the initial batch processing.

Also, the inclusion of wax retards air treatment chemical volatization prior to burning, and thus less expensive packaging can therefore be used. Further, placing the air treatment chemical only at the peripheral surface can avoid air treatment chemical being destroyed/degraded by too prolonged exposure to heat prior to escaping the interior of the coil.

The foregoing and other advantages of the present invention will be apparent from the following description. In the description that follows reference is made to the accompanying drawings which form a part thereof, and in which there is shown by way of illustration, and not limitation, preferred embodiments of the invention. As these embodiments are merely illustrative, they are not intended to represent the full scope of the invention. Thus, reference should therefore be made to the claims herein for interpreting the scope of the invention.

DETAILED DESCRIPTION OF THE INVENTION

Figure 1:
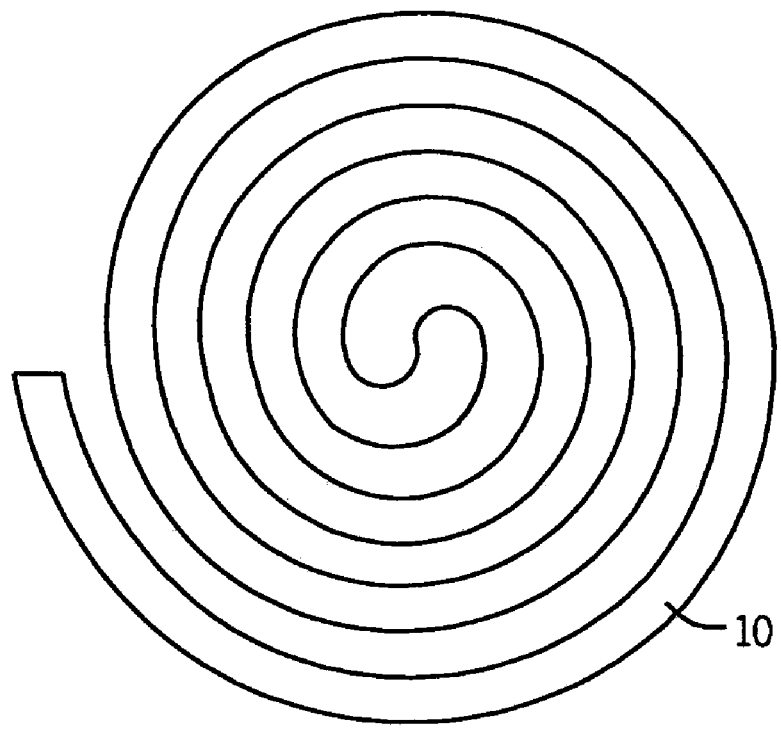
FIG. 1 is a top plan view of a first embodiment of the present invention in the form of a mosquito coil.
Figure 2:
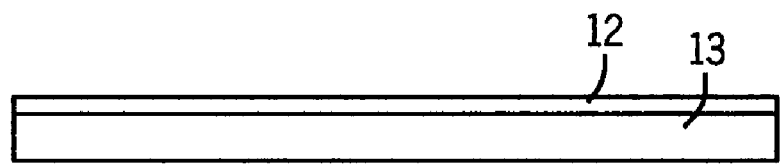
FIG. 2 is a front elevational view thereof.

A base portion of preferred substrates, in the form of mosquito coils, can be manufactured by first preparing a wet dough. To do this one can create a cooked starch intermediate, a powder portion, and (if the air treatment chemical is to be mixed in with the dough) an air treatment chemical/solvent mix.

One way of forming the starch intermediate is to add cold water (15° C. to 27° C.) to a vessel. The water is then agitated using a diaphragm pump while adding minor amounts of a preservative like sodium benzoate, a dye and a starch binder. This is then heated to about 90° C. while continuing liquid agitation, for 30 minutes.

One can then separately grind a cellulosic powder and make sure that the powder is within a specified particle/mesh size, determined based on desired burning time and other optimization parameters.

Then, one can separately obtain the desired solvent/air treatment chemical mix, by purchasing it or diluting a concentrate.

One can then mix the cellulosic powder, the air treatment chemical/solvent (when it is to be added to the dough), and the cooked starch intermediate. A jacketed (steam/water), double ribbon blender with chopper blade can be used for this purpose or a kneader type paste mixer can be used.

It is preferred to extrude the paste into a board. One can use a variable speed extruder unit with a feed/breaker that helps the material to be fed into the screw. The extruder barrel can be jacketed to provide temperature control of the material as it is extruded. Extrusion begins by pouring the mixed material which is at a temperature of approximately 45° C. to 50° C. into the feed hopper. Jacket temperature for the extruder barrel is set to approximately 30° C. to cool the material somewhat as it passes through the extruder and reduce tearing of the material as it exits the die head. In one process the paste is extruded at approximately three feet per minute.

Once extruded one can use a stamping process to cut the coil shapes out of the dough. The paste should be stamped as soon as possible after extrusion.

In one process the extruder places the board on a conveyor which is set at a speed coordinated with the output of paste from the extruder. A stamping head/die/cutting head cuts the dough into specified shapes. If desired, a silicone release compound can be placed on the conveyor.

Freshly stamped coils are then placed on racks which have mesh drying screens made of coated nylon. The drying racks are then placed in an enclosed drying room and heated to about 40° C. with an electric fan circulating air. In about eight hours the dough is dried to have roughly 5% moisture.

In an alternative process the drying temperature is 60° C. for 180 minutes. Other combinations of temperature and drying time are possible as well.

Where the wax has not been pre-mixed into the main dough (which is the most preferred approach) a top coating thereof (or even better of a mix of the wax plus air treatment chemical) can be applied with a roller to a top surface of the coil after the initial drying step. See e.g. U.S. Pat. No. 6,419,898 for a discussion of roller techniques as applied to prior art mosquito coils.

Examples of various coating layers 12 that were prepared have the following formulas before air treatment chemical was added:

(a) 64.82% deionized water, 27.19% AC-316 polyethylene wax (from Honeywell), 6.8% Neodol® 25-9 linear ethoxylated alcohol, 0.87% 45% solution of KOH, 0.32% sodium metabisulfite, and 0.02% Kathon® preservative.

(b) 64.32% deionized water, 27.19% AC-316, 3.47% Neodol® 25-9, 3.33% oleic acid, 0.87% 45% KOH, 0.5% ammonia, 0.32% sodium metabisulfite and 0.02% Kathon®.

(c) 64.12% deionized water, 27.19% AC-316, 6.8% oleic acid, 0.87% 45% KOH, 0.7% ammonia, 0.32% sodium metabisulfite and 0.02% Kathon®.

(d) 64% tap water, 28% AC-316 polyethylene wax (from Honeywell), 7% $C_{13-15}$ ethoxylated alcohol, 0.9% 50% solution of KOH, and 0.01% Bodoxin® preservative.

It is preferred to use a wax emulsion, rather than wax per se, to facilitate automated production. Of course, the rolling process could be replaced with other application techniques such as a spraying or dipping process.

Other forms of cellulosic main bodies are possible as well. Instead of using a dough based coil, one could use a paper based coil, and apply the wax/air treatment chemical thereon.

In the above examples the oxidized polyethylene wax AC-316 has a low acid number between 16 and 18. Other suitable oxidized polyethylene waxes have a higher acid number. In any event, it is desirable that the wax have some acid groups so as to be more readily emulsifiable in water when any emulsion is used. Numerous waxes of this type appear suitable, such as Honeywell's AC-392, AC-325, AC-540, Clariant's PED 152, Eastman's E-20 and BASF's OA3. For example, polypropylene-based waxes such as Eastman's E-43, and blends of such polypropylene-based and polyethylene-based waxes could instead be used. Further even natural waxes appear suitable (e.g. beeswax) for some applications.

To understand the chemistry of the most preferred emulsions consider the following reaction where R is the oxidized polyethylene and the end of the reaction creates the emulsified wax:

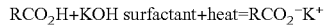

$$RCO_2H + KOH \text{ surfactant} + \text{heat} = RCO_2^- K^+$$

The potassium hydroxide in the preferred formulas neutralizes the acidic sites of the wax. As can be seen from alternative formulas below, other bases can instead be used including ammonia, DEEA (N,N-diethylaminoethanol), DMEA (N,N-dimethylaminoethanol), NaOH, and others.

Kathon® is a biocide preservative containing 5-chloro-2-methyl-4-isothiazolin-3-one and 2-methyl-4-isothiazolin-3-one. Other preservatives such as Bodoxin and formaldehyde could also be used.

A preferred surfactant, Neodol® 25-9, is a 9 mole ethylene oxide adduct of a $C_{12}$ to $C_{15}$ primary alcohol mixture. A formula therefor is $RCH_2-O-(CH_2CH_2O-)_9-H$ where R is an alkyl chain of 11 to 14 carbons.

Shorter and longer hydrophobic chains will also work. Slightly shorter and longer ethylene oxide chains will also work. There are numerous other nonionics that would be suitable such as secondary alcohol ethoxylates (e.g. Tergitol® 15S-9).

In one example, using a pressure reactor, hot water (2.593#) was mixed with Neodol® 25-9 (0.68#), 45% KOH (0.087#) and sodium metabisulfite (0.032#). Wax flakes or pellets (e.g. oxidized polyethylene such as AC-316) (2.719#) were added with mixing. The pressure reactor was sealed and heated above the melt point of the wax such as 82 to 88° C.

In a separate vessel, steam (water at or near boiling pt., 3.589#) was pumped into the wax reactor under pressure which caused a temperature drop. The vessel was heated to 82 to 88° C. and maintained for about 5 minutes. The mixture was immediately cooled under continued agitation to room temperature. The wax emulsion was filtered and solids determined. The solids were adjusted with the remaining water and Kathon® (0.002#) was added as a preservative. The air treatment chemical/solvent can be mixed in to the emulsion shortly before application to the dough.

The wax emulsion can be anionic, or a combination of anionic and nonionic. The desired result is a low cost emulsion that dries to a wax.

As one example the emulsion was mixed with 0.20% of allethrin/pynyamin forte, and a layer of the resulting mixed emulsion was then rolled onto base 13. The resulting structure was dried a bit further, albeit this last step could be eliminated if desired if the water content of the emulsion is kept low.

Figure 4:
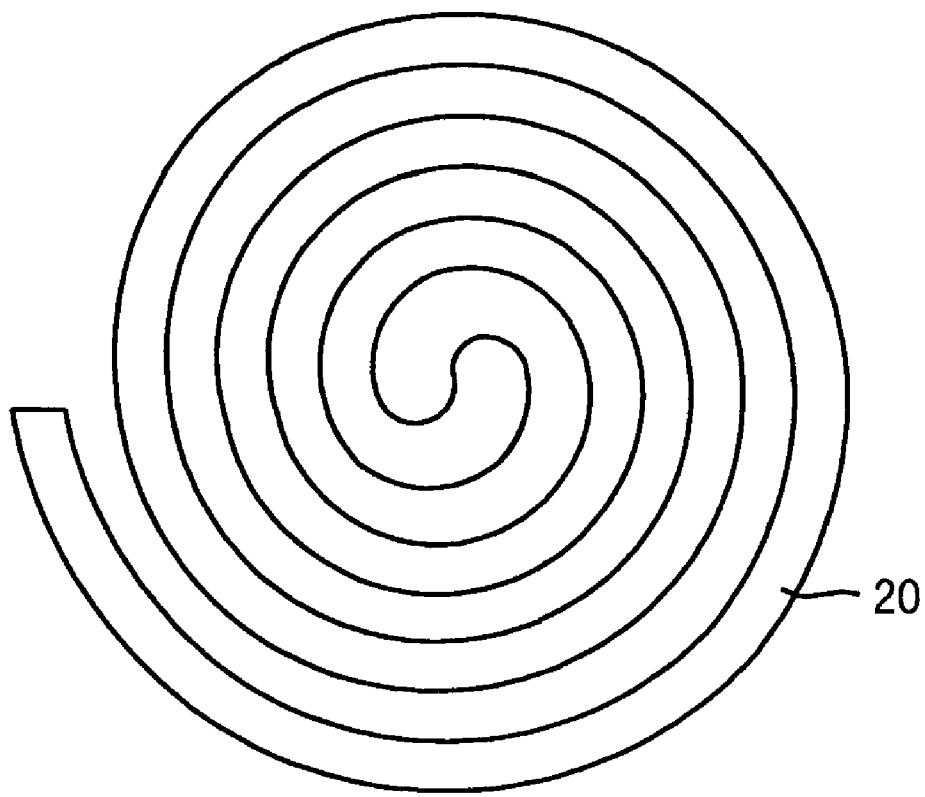
FIG. 4 is a top plan view similar to FIG. 1, but of a second embodiment, where the air treatment chemical and wax are uniformly mixed in the main body, rather than in a separate layer placed on the base.
Figure 5:
FIG. 5 is a front elevational view thereof.

Alternatively, the wax and air treatment chemical can instead be mixed into the dough before board formation to yield coil 20 in FIGS. 4 and 5 having a top peripheral surface 22.

Testing

Figure 3:
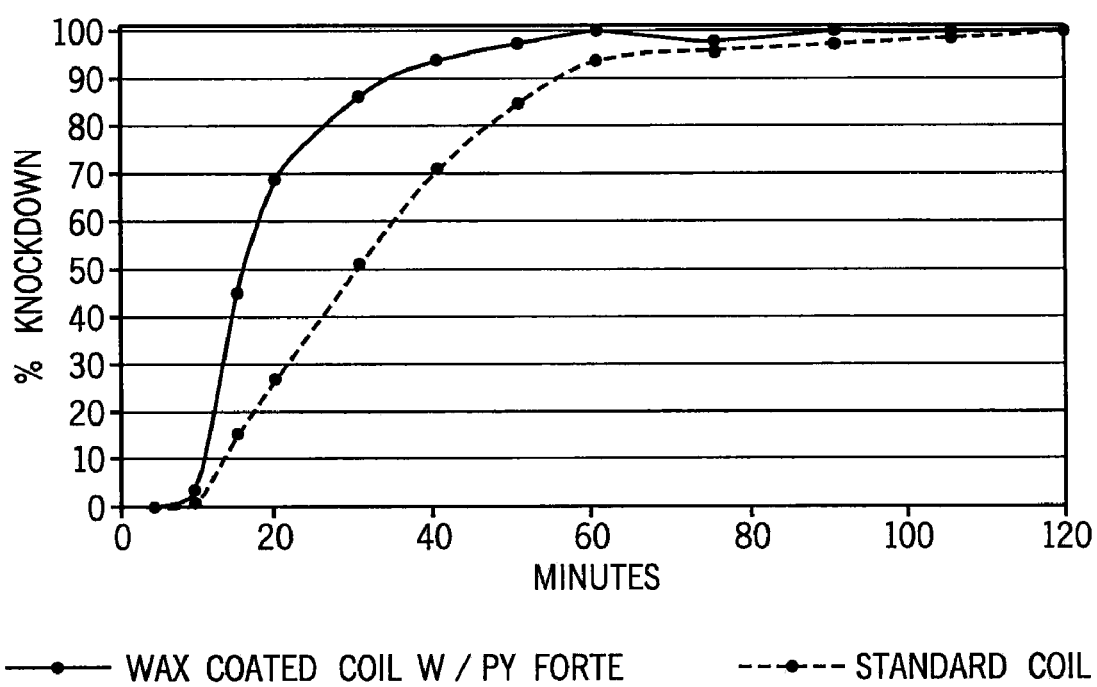
FIG. 3 is a graph showing experimental results comparing use of a FIG. 1 coil to a prior art coil.

The coils were then tested in comparison to prior art coils by evaluating mosquito knockdown efficiency. Representative test results are depicted in FIG. 3. As can be seen, the knockdown using the waxed coil was much quicker (when both wax and the active were part of a coating), indicating that identical performance could be achieved with less pynamin forte concentration, or a smaller coil. Similar results were obtained for varied insect control actives and different types of mosquitoes.

These effects are believed to be largely due to avoiding premature air treatment chemical loss during drying, and to avoiding air treatment chemical degradation.

Adding the wax uniformly throughout the body was also tried. This slowed the burn rate, but resulted in reduced knockdown.

Wax melting points between 65° C. and 121° C. (150° F.-250° F.) are preferable, with melting points below 93° C. (200° F.) most preferred. In this regard, waxes with too high a melting point will tend to snuff the burning coil, and waxes with too low a melting point will melt prior to use in some climates.

While the preferred embodiments have been described above, it should be appreciated that there are numerous other embodiments of the invention within the spirit and scope of this disclosure. For example, the substrate need not be coil shaped, and even when a coil is presented it need not have a circular spiral top view shape. Instead, the coil may be a rectangular spiral, or the entire substrate may be straight (e.g. like a punk), or have other shapes. Further, while the primary intended utility is for mosquito control, such devices can also be used to control other insects and/or dispense fragrances. Hence, the invention is not to be limited to just the specific embodiments shown or described.

INDUSTRIAL APPLICABILITY

Disclosed herein are improved air treatment chemical dispensing substrates, such as mosquito coils, and methods for creating them.

What is claimed is:

1. An air treatment chemical dispensing substrate in the form of a spiral coil that is configured for dispensing the air treatment chemical by burning the substrate, the coil comprising a burnable body having at least 89% by weight of non-wax base material, between 0.05% and 10% by weight of wax, and an air treatment chemical to be dispensed by the substrate;

wherein there is such air treatment chemical in a coating portion of the spiral coil, and an internal portion of the spiral coil has no wax or a reduced concentration of wax relative to a concentration thereof at a top peripheral surface of the coil;

wherein said coating also comprises an emulsifier and the wax; and wherein the wax is an oxidized wax with acid groups that have been neutralized with a base.

2. The substrate of claim 1, wherein the air treatment chemical is selected from the group consisting of insect control actives and fragrances.

3. The substrate of claim 2, wherein the air treatment chemical is an insect control active.

4. The substrate of claim 3, wherein the insect control active is a mosquito control active.

5. The substrate of claim 1, wherein the substrate comprises at least 98% of non-wax base material which is cellulosic.

6. The substrate of claim 5, wherein the body is in a form of cellulosic paper.

7. The substrate of claim 1, wherein the air treatment chemical is present in at least 0.0001% by weight and is less than 2% by weight.

8. The substrate of claim 1, wherein the wax is selected from the group consisting of base neutralized oxidized polyethylene waxes and base neutralized oxidized polypropylene waxes.

9. The substrate of claim 1, wherein the substrate has been formed by creating a wet version of an internal portion thereof, at least partially drying said wet version, coating said at least partially dried wet version with a mixture of said wax, air treatment chemical, surfactant and water to create a coated substrate, and then at least partially drying said coated substrate.

10. The substrate of claim 1, wherein the substrate is in the form of an insect control coil.

* * * * *